(12) United States Patent
Lee et al.

(10) Patent No.: US 9,326,940 B2
(45) Date of Patent: May 3, 2016

(54) ASYMMETRIC LIPOSOMES FOR THE HIGHLY EFFICIENT ENCAPSULATION OF NUCLEIC ACIDS AND HYDROPHILIC ANIONIC COMPOUNDS, AND METHOD FOR PREPARING SAME

(75) Inventors: Myung Kyu Lee, Daejeon (KR); Abbas Mokhtarieh Amir, Daejeon (KR); Bong Hyun Chung, Daejeon (KR); Jong Min Choi, Daejeon (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 802 days.

(21) Appl. No.: 13/697,705

(22) PCT Filed: Nov. 12, 2010

(86) PCT No.: PCT/KR2010/007994
§ 371 (c)(1),
(2), (4) Date: Feb. 1, 2013

(87) PCT Pub. No.: WO2011/142515
PCT Pub. Date: Nov. 17, 2011

(65) Prior Publication Data
US 2013/0149374 A1    Jun. 13, 2013

(30) Foreign Application Priority Data
May 14, 2010    (KR) .................. 10-2010-0045399

(51) Int. Cl.
| A61K 9/127 | (2006.01) |
| A61K 31/122 | (2006.01) |
| A61K 31/70 | (2006.01) |
| A61K 31/713 | (2006.01) |

(52) U.S. Cl.
CPC ............ *A61K 9/1272* (2013.01); *A61K 9/1271* (2013.01); *A61K 9/1277* (2013.01); *A61K 31/122* (2013.01); *A61K 31/70* (2013.01); *A61K 31/713* (2013.01)

(58) Field of Classification Search
CPC .................................................. A61K 9/127
See application file for complete search history.

(56) References Cited

U.S. PATENT DOCUMENTS

| 6,056,973 | A | * | 5/2000 | Allen | .............. | A61K 9/127 |
| | | | | | | 424/450 |
| 6,288,130 | B1 | * | 9/2001 | Heidlas | ............. | A23J 7/00 |
| | | | | | | 426/662 |
| 7,005,140 | B2 | * | 2/2006 | Zhang | ............. | A61K 47/48815 |
| | | | | | | 424/450 |
| 7,491,409 | B1 | * | 2/2009 | Meers | ................. | A61K 9/127 |
| | | | | | | 264/4.1 |
| 2003/0152618 | A1 | * | 8/2003 | Fisher | ............... | A61K 49/1812 |
| | | | | | | 424/450 |
| 2006/0165773 | A1 | * | 7/2006 | Perez-Soler | ......... | A61K 9/1272 |
| | | | | | | 424/450 |

FOREIGN PATENT DOCUMENTS

JP        EP 2008710 A1 * 12/2008  ........... A61K 9/1277

OTHER PUBLICATIONS

Radchatawedchakoon et al. (2010). "Solid phase synthesis of novel asymmetric hydrophilic head cholesterol-based cationic lipids with potential DNA delivery." Bioorganic & Medicinal Chemistry, 18: 330-342.*
Cans et al. (2008), "Positioning Lipid Membrane Domains in Giant Vesicle by Micro-organization of Aqueous Cytoplasm Mimic", J. Am. Chem. Soc., 130: 7400-7406.
Franzin et al. (1997), "Detection and Quantification of Asymmetric Lipid Vesicle Fusion Using Deuterium NMR", Biochemistry, 36: 2360-2370.
Puyal et al. (1995), "A new cationic liposome encapsulating genetic material. A potential delivery system for polynucleotides", Eur. J. Biochem., 228: 697-703.
Matthay et al. (1989), "Role of Ligand in Antibody-directed Endocytosis of Liposomes by Human T-Leukemia Cells," Cancer Research 49, 4879-4886.
Radchatawedchakoon (2010), "Solid phase synthesis of novel asymmetric hydrophilic head cholesterol-based cationic lipids with potential DNA delivery", Bioorganic & Medicinal Chemistry 18; 330-342.
International Search Report dated Jul. 29, 2011, for International Application No. PCT/KR2010/007994.

* cited by examiner

Primary Examiner — Frederick Krass
Assistant Examiner — Amanda Heyes
(74) Attorney, Agent, or Firm — Lathrop & Gage LLP

(57) ABSTRACT

The present invention relates to asymmetric liposomes for high encapsulation efficiency of nucleic acids and hydrophilic anionic compounds, and to a method for preparing same, and specifically, to asymmetric liposomes consisting of a cationic lipid having a small head group as an internal lipid and a neutral or PEGylated lipid having a big head group as an external lipid, wherein nucleic acids and/or anionic compounds are encapsulated in the internal lipid. According to the present invention, asymmetric liposomes, in which nucleic acids and hydrophilic anionic compounds are encapsulated with high efficiency, may be prepared, and thus the same may be used for various purposes, such as gene therapy, and the delivery of hydrophilic anionic drugs which are difficult to prepare as prodrugs, and drug delivery, imaging, etc. can be carried out by encapsulating a fluorescent contrast agent in the liposome.

11 Claims, 20 Drawing Sheets

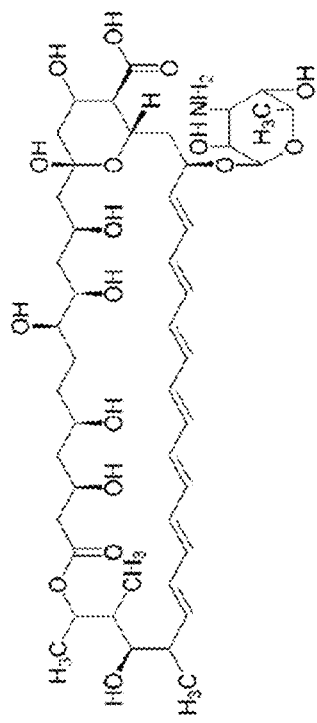
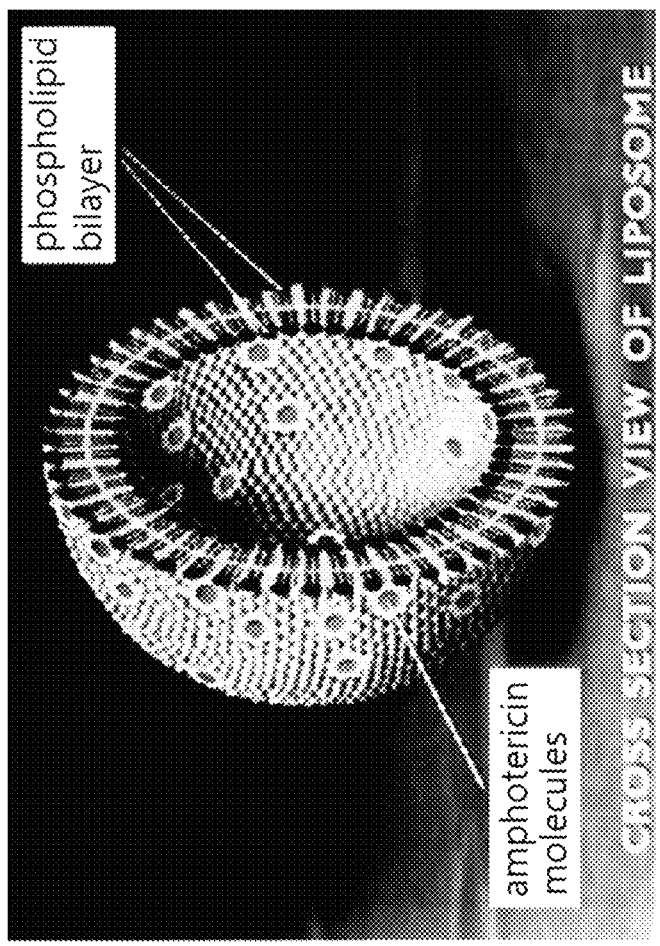
Fig. 1
PRIOR ART

Fig. 2
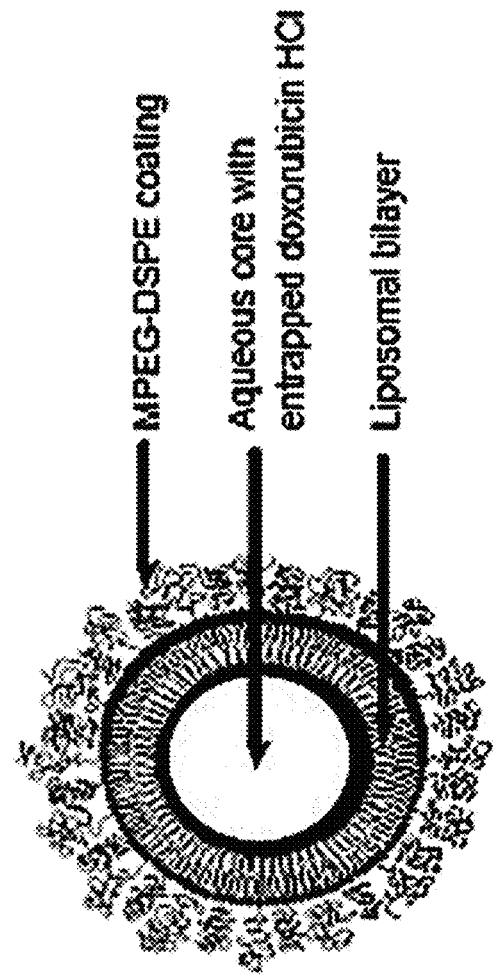
PRIOR ART
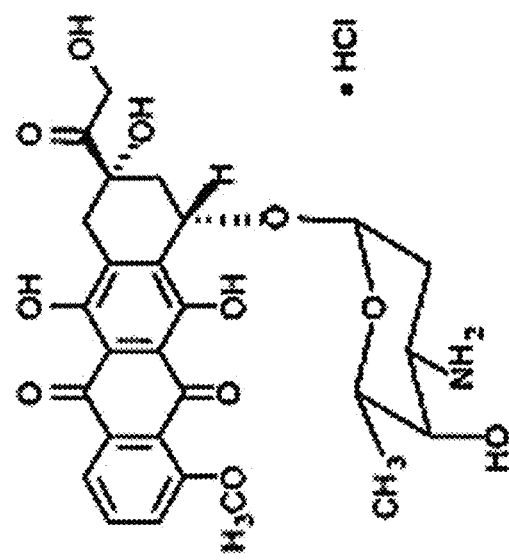

NCI-H322

NCI-H322

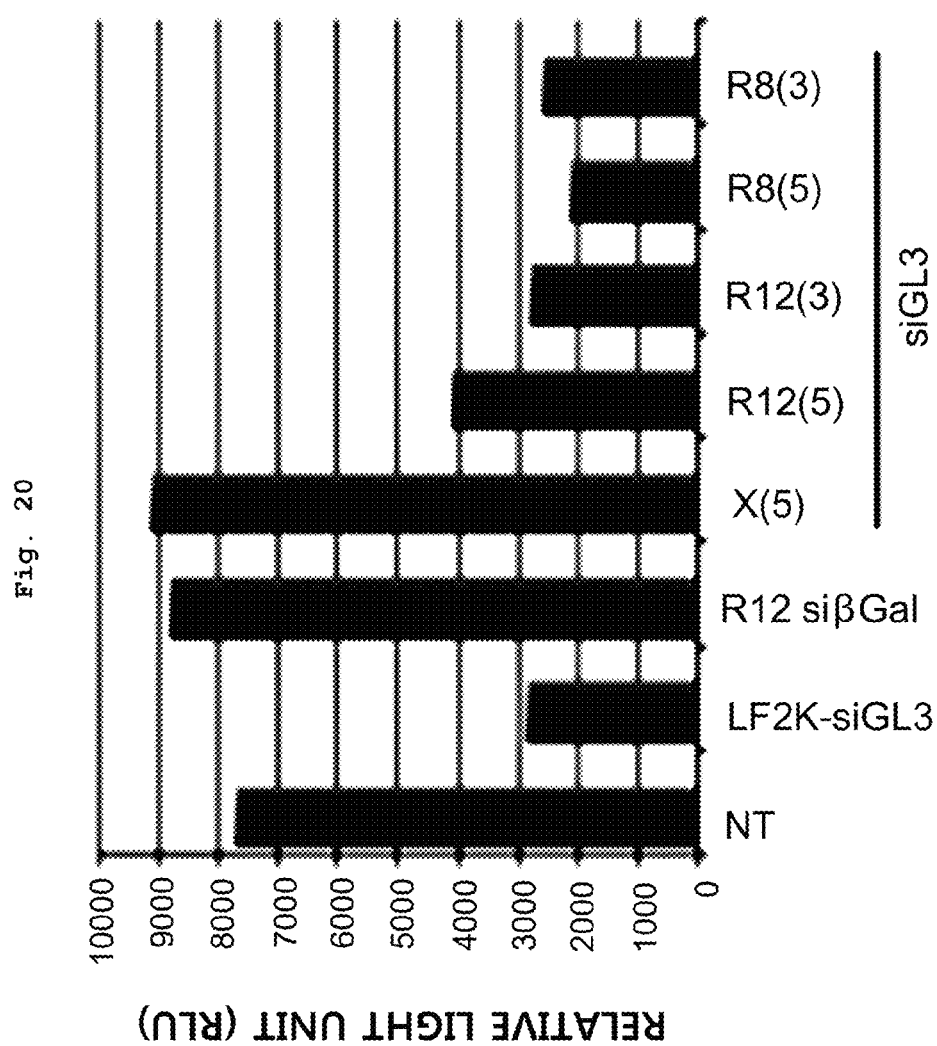

ASYMMETRIC LIPOSOMES FOR THE HIGHLY EFFICIENT ENCAPSULATION OF NUCLEIC ACIDS AND HYDROPHILIC ANIONIC COMPOUNDS, AND METHOD FOR PREPARING SAME

CROSS-REFERENCE TO RELATED APPLICATIONS

This application is a U.S. National Stage Application under 35 U.S.C. §371 of International Application No. PCT/KR2010/007994, filed Nov. 12, 2010, which claims the benefit of Korean Application No. 10-2010-0045399, filed May 14, 2010. Both of these applications are hereby incorporated by reference in their entireties.

BACKGROUND

1. Field of the Invention

The present invention relates to an asymmetric liposome for highly efficient encapsulation of nucleic acid and hydrophilic anionic compound and a preparation method thereof.

2. Description of the Related Art

Drug delivery system (DDS) that effectively delivers necessary amounts of drug without causing side effect and provides maximized efficacy and effect of the drug is one of the high value core technologies with high possibility of success which can create economic profit comparable to that made by new drug development and improve quality of patients' lives.

Solubilization of non-soluble drug, which facilitates drug absorption, is one of the core technologies of DDS and is currently considered the most reasonable way to decrease cost for developing new substances and increase value of pharmaceutical products. Particularly in South Korea, environments are not supportive to developers of new drugs. The advanced solubilization technology will create tremendous values with relatively small investment by developing modified new drugs (KAIST Annual Report on Technology Trend, 2004).

Liposome is one of the most widely used substance that is used in the delivery of genes or drugs.

Liposome is a lipid-bilayer vesicle formed of phospholipid of amphipathic lipid cell layer as a main component, and used for drug delivery by encapsulating soluble drug in aqueous compartment or carry the hydrophobic drug in lipid-bilayer. The layer structure of the liposome is similar to that of cell layer and has small toxicity. Accordingly, drug delivery is possible via fusion with cells or introduction into cell. Further, depending on combination, properties including sizes, surface potential or chemical modifications are adjustable. Further, the excellent biocompatibility is the reason for active efforts to develop liposome as a drug delivery substance (Bangham, Torchilin, V. P. 2005, *Nat. Rev. Drug Discov.*, 4; 145).

An example of commercialized liposomal drug is Ambisome® developed to treat indication of mycotic infection by the association of Gilead (USA) and Fujisawa (Japan) (FIG. 1). Ambisome® is prepared by introducing amphotericin, which is the mycotic infection treating agent, into the unilamellar bilayer of approximately 100 nm liposome by the hydrophilic attraction with long-chain alkyls of phospholipid, and adding components including hydrogenated soy phosphatidylcholine (HSPC), cholesterol, distearoylphosphatidyl glycerol (DSPG), antioxidant, anti-coagulating agent, or the like and then lyophillizing (US FDA product information Amphotericin).

Like other particulate DDS for use in systemic circulation, liposomes have shortcomings that these are lost in the circulatory system due to phagocytosis of macrophagocyte prevalently existing in the livers or spleens due to adsorption of proteins in the blood or spillage of the drug from the liposomes during circulation in the blood. The phagocytosis of macropagocyte is of particular concern, because this induces adsorption of opsonic protein on the surfaces of liposomes. To solve the above-mentioned shortcomings, it was suggested to suppress adsorption of opsonic protein by using phospholipid-PEG derivative having PEG(poly[ethylene glycol]) bound to the terminus of phosphatidylethanolamine, or coating the surface of the prepared liposome with PEG or multisaccharides. These liposomes prolong drug circulation time in the blood by reducing loss of drug by the phagocytosis of macropagocyte, and furthermore, enhances arrival rate of the drug to the targeting organs. The 100 nm sized PEG-liposome technology developed by Alza (USA), so-called stealth liposome, was commercialized in the form of liposomal anticancer agent with increased circulation time in the blood. Ortho Biotech (USA) commercialized Doxil, the result of applying the stealth-liposome technology to doxorubicin, the anthracyclinc family anticancer agent (US FDA product information Doxil).

The nucleic acid such as antisense RNA or siRNA has gained attention as an important tool for the treatment of cancer, genetic disease, infectious disease, autoimmune disorder, etc., for its property to inhibit expression of specific proteins in living body (Novina and Sharp, *Nature*, 430, 161-164, 2004). However, many researches are conducted to overcome the shortcomings of using nucleic acid such as siRNA, such as difficulty of direct delivery into cells and easy disruption by enzyme in the blood.

Recently, the method for delivering nucleic acid into cells include mixing with positively-charged lipid (lipid-DNA complex or lipoplex) and mixing with polymer (polymer-DNA complex or polyplex) (Hirko et al., *Curr. Med. Chem.*, 10, 1185-1193, 2003; Merdan et al., *Adv. Drug. Deliv. Rev.*, 54, 715-758, 2002; Spagnou et al., Biochemistry, 43, 13348-13356, 2004). Lipid-DNA complex is widely used at a cellular level because this binds to nucleic acid to facilitate delivery of nucleic acid into the cell. However, lipid-DNA complex in many cases induces inflammation in vivo when injected locally (Filonand and Phillips, *Biochim. Biophys. Acta*, 1329, 345-356, 1997), and accumulates in the organs on the passage when intravascular-injected (Ren et al., Gene Therapy, 7, 764-768, 2000). On the contrary, because phospholipid existing in vivo is neutral or negatively-charged, it has considerably low affinity to nucleic acid.

One suggestion to solve the above-mentioned drawback is to join another lipid such as cholesterol to the sense strand of siRNA for delivery thereof. However, because these complexes are joined with lipoprotein such as LDL and HDL in the blood and delivered, the complexes mainly have liver tissue specificity (Soutschek et al., Nature, 432, 173-178, 2004; Wolfrum et al., Nat. Biotechnol., 25, 1149-1157, 2007).

Further, polyplex, in which nucleic acid is joined with cationic polymer, has the shortcoming of low delivery rate to an intended tissue due to reasons such as removal by the complement, etc. (Plank et al., *Human Gene Ther.*, 7, 1437-1446, 1996; Chui et al., *Chem. Biol.*, 11, 1165-1175, 2004; Elmen et al., nucleic *Acids Res.*, 33, 439-447, 2005).

Additionally, siRNA exposure acts as an agonist to the toll-like receptor and thus non-specifically increases interferon alpha expression (Hornung et al., Nat. Med., 11, 263-270, 2005) or induces non-specific innate immune reaction (Judge et al., Nat. Biotech., 23, 457-462, 2005).

It was suggested that siRNA stability can be improved and non-specific immune reaction can be removed by substituting 2'-OH of siRNA with 2'-F, 2'-OMe and 2'-H (Morrissey et al., Hepatology, 41, 1349-1356, 2005), but the cost for synthesis is huge and it is necessary to prepare lipoplex and polyplex to ensure delivery.

Because hydrophilic anionic drug hardly penetrates cells, a medicine developed with this hydrophilic anionic drug is generally made in the form of prodrug capable of cell permeation. Further, hydrophilic anionic fluorescence substance such as calcein, indocyanine green, or chlorotoxin (Cy5.5) can be used as an important imaging tool to measure movement of liposome in the body.

To encapsulate nucleic acid with strong anionic property into liposome, the lipid mixture containing cationic lipid is generally utilized. Among the currently developed methods, the methods with relatively high encapsulation rate of polymer nucleic acid include agitation using ultrasonic waves with the use of EPC/CH/lysine-DPPE (Encapsulation rates of various nucleic acids, 60-100%) (Puyal et al., Eur. J. Biochem. 15, 697-703, 1995), detergent dialysis using DOPE/PEG-Cer/DODAC (4-10 Kbp, encapsulation rate, 60-70%) (Wheeler et al., Gene Ther., 6, 271-281, 1999), ethanol dialysis using (DODAP/Chol/DSPC/PEG-cer or DSPC/Chol/PEG-C-DMA/DLinDMA (ODN encapsulation rate 50% or siRNA encapsulation rate 93%) (Semple, 2001 Biocheim. Biophys. Acta, 1510; 152-166; Morrissey, 2005, Nat. Biotech., 23; 1002-1007), hydrolysis of lyophilized matrix using DOTAP/Chol/DOPE/PEG-cer (siRNA encapsulation rate, 95%) (Wu et al., Pharm. Res., 26, 512-522, 2009) and many others. However, because all these methods encapsulate nucleic acid by use of one common composition of lipoplex in the preparation thereof, it is difficult to encapsulate low molecular hydrophilic anionic substance effectively.

Accordingly, the inventors of the present invention prepared asymmetric liposome having an interior consisting of a cationic lipid which is toxic internally but is advantageous for the purpose of encapsulating nucleic acid and hydrophilic anionic compound, and has a small head group to enable desirable placement within liposome, and an exterior consisting of a neutral and anionic lipid with similarity to cell surface and thus is less toxic, and completed the present invention by confirming that the liposome prepared as explained above can encapsulate siRNA and hydrophilic anionic compound.

SUMMARY

Exemplary embodiments of the present inventive concept overcome the above disadvantages and other disadvantages not described above. Also, the present inventive concept is not required to overcome the disadvantages described above, and an exemplary embodiment of the present inventive concept may not overcome any of the problems described above.

A technical object is to provide an asymmetric liposome for highly efficient encapsulation of nucleic acid and hydrophilic anionic compound and a preparation method thereof.

In order to achieve the above-mentioned object, the present invention provides an asymmetric liposome including a cationic lipid having a small head group as an internal lipid and a neutral or PEGylated lipid having a big head group as an external lipid, wherein nucleic acids and/or anionic compounds are encapsulated in the internal lipid.

Further, the present invention provides a method of preparing an asymmetric liposome, which may include steps of: preparing an internal inverted micelle encapsulating nucleic acid or hydrophilic anionic compound in a cationic lipid by use of ether/buffer solution mixture liquid (step 1), preparing an external inverted micelle with respect to a neutral lipid and PEGylated lipid by use of ether/alcohol/buffer solution mixture liquid (step 2), and preparing an asymmetric liposome encapsulating therein the nucleic acid or hydrophilic compound by mixing the internal inverted micelle and the external inverted micelle respectively prepared at steps 1 and 2, evaporating organic solvent, and performing dialysis (step 3).

Because asymmetric liposome encapsulating therein nucleic acid and hydrophilic anionic compound with high efficiency can be prepared, an embodiment can be applied for various purposes including genetic treatment, and drug delivery or imaging using hydrophilic anionic drug delivery and fluorescent contrast agent, which are generally hardly prepared into prodrug.

BRIEF DESCRIPTION OF THE DRAWINGS

The above and/or other aspects of the present inventive concept will be more apparent by describing certain exemplary embodiments of the present inventive concept with reference to the accompanying drawings, in which:

FIG. 1 shows a chemical structure of a conventional mycotic infection treating agent, Amphotericine B, and cross-section view of Ambisome®.

FIG. 2 shows a chemical structure of a conventional anti-cancer treatment, Doxorubicin, and a cross-section of Doxil.

FIG. 16e is an enlarged image of FIG. 16d.

FIG. 17e is an enlarged image of FIG. 17d.

FIG. 20 is a graph showing the cell permeability of the anti-GL3 luciferase siRNA (siGL3)-encapsulating liposome, with the surface being labeled with R8 and R12 peptides.

DETAILED DESCRIPTION OF EXEMPLARY EMBODIMENTS

Figure 3:
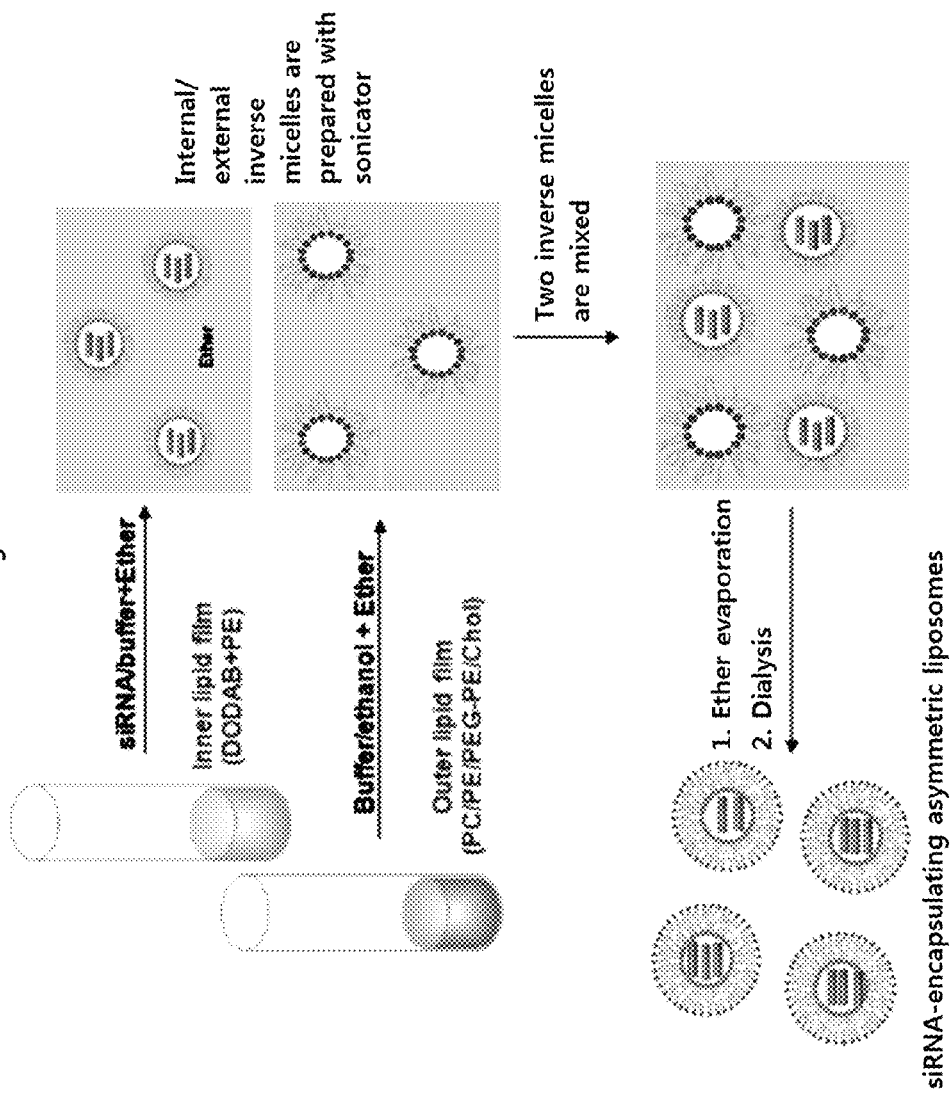
FIG. 3 illustrates a method of preparing asymmetric liposome to encapsulate nucleic acid and hydrophilic anionic compound with high efficiency, according to the present invention.

Certain exemplary embodiments of the present inventive concept will now be described in greater detail with reference to the accompanying drawings.

An embodiment provides an asymmetric liposome including a cationic lipid of a small head group as an internal lipid and a neutral or PEGylated lipid of a big head group as an external lipid, in which nucleic acid and/or anionic compound are encapsulated in the internal lipid.

In the asymmetric liposome according to an embodiment, the internal lipid is highly toxic due to use of cationic lipid, but is more advantageous in the aspect of encapsulation of nucleic acid and hydrophilic anionic compound due to small head group thereof. That is, because of the small head group, the internal lipid can be well placed in the liposome. On the other hand, the external lipid using neutral or anionic lipid has big head group, and thus is more advantageous to be placed outside the liposome. Because the external lipid is similar to the surface of the cell, the external lipid does not non-specifically bind to the proteins and cells in the blood.

In one embodiment, the hydrophilic anionic compound includes drug, fluorescent substance for diagnosis, or the like.

In one embodiment, the internal lipid may preferably use a component including dioleoyl dimethylammonium propane (DODAP) and dioleoyl phosphatidylethanolamine (DOPE) or dipalmitoylphosphatidylethanolamine (DPPE), with molar ratio of DODAP and DOPE or DPPE ranging between 1:1 and 9:1.

In one embodiment, the external lipid may preferably include neutral phospholipid, PEGylated phospholipid (PEG-PE) and cholesterol, in which the neutral phospholipid may preferably be selected from the group consisting of DPPE/DOPE, DSPC/DPPE or DSPC/DOPE, and more preferably be DSPC/DOPE. The molar ratio of the neutral phospholipid may preferably be less than 1/2 per the entire external lipid, and the molar ratio of DPPE/DOPE, DSPC/DPPE or DSPC/DOPE may preferably range between 1:1-3:0. Further, the cholesterol content may preferably be 1/3 or above with respect to the entire external lipid.

In the asymmetric liposome according to the present invention, the PEGylated phospholipid (PEG-E) content to the entire external lipid may preferably range between 1/6 and 1/4.

According to the present invention, a function group may be attached to a surface of the asymmetric liposome for the purpose of cell target-oriented transmission and cell permeation. The function group may include antigen, peptide or low molecular ligand. A functional PEGylated phospholipid may additionally be attached to attach the function group. For the functional PEGylated phosopholipid, maleimide -PEG-PE (miPEG-PE), or carboxylic-PEG-PE (caPEG-PE) may be used, but not limited thereto. The functional PEGylated phospholipid content may preferably equal to or less than 1/60 of the entire external lipid.

According to the present invention, the negative ion/positive ion (N/P) ratio of the nucleic acid and the cationic lipid may preferably equal to or less than 1:2. Above this ratio, nucleic acid encapsulation rate decreases.

Furthermore, according to the present invention, the mole ratio between the entire internal lipid of the asymmetric liposome and the external lipid may preferably be 1:1.2.

Further, according to the present invention, a method of preparing an asymmetric liposome is provided, which may include preparing an internal inverted micelle encapsulating nucleic acid or hydrophilic anionic compound in a cationic lipid by use of ether/buffer solution mixture liquid (step 1), preparing an external inverted micelle with respect to a neutral lipid and PEGylated lipid by use of ether/alcohol/buffer solution mixture liquid (step 2), and preparing an asymmetric liposome encapsulating therein the nucleic acid or hydrophilic compound by mixing the internal inverted micelle and the external inverted micelle respectively prepared at steps 1 and 2, evaporating organic solvent, and performing dialysis (step 3).

The step 1 prepares an internal inverse micelle encapsulating nucleic acid and/or hydrophilic anionic compound in the auctioning lipid by use of a mixed solution of ether/buffer solution. To be specific, the internal inverse micelle may be prepared by suspending cationic lipid and nucleic acid and/or hydrophilic anionic material in buffer solution pH 4, adding ether and stirring by a sonicator.

For the internal lipid, dioleoyl dimethylammonium-propane (DODAP) and dioleoyl phosphatidylethanolamine (DOPE) or dipalmitoylphosphatidyl ethanolamine (DPPE) may preferably be used, in a mole ratio of DODAP and DOPE or DPPE preferably ranging between 1:1 and 9:1.

According to the present invention, the N/P ratio of nucleic acid and cationic lipid may preferably equal to or less than 1:2.

According to the method of the present invention, the hydrophilic anionic compound and nucleic acid may be encapsulated individually or simultaneously.

Next, the step 2 prepares the external inverse micelle with respect to the neutral lipid and PEGylated lipid, by use of a mixed solution of ether/alcohol/buffer solution. To be specific, the external inverse micelle may be prepared by adding and suspending neutral lipid and PEGylated lipid to alcohol and buffer solution, adding ether and stirring with ultrasonic waves.

The alcohol may be ethanol or methanol, and the mixed solution of alcohol and buffer solution may preferably be mixed with a ratio ranging between 2:1 and 1:1.

According to the preparation method of the present invention, the external lipid includes a neutral phospholipid, PEGylated phospholipid (PEG-PE) and cholesterol. The neutral phospholipid may preferably be selected from the group consisting of DPPE/DOPE, DSPC/DPPE or DSPC/DOPE, and more preferably, may be DSPC/DOPE. The molar ratio of the total neutral phospholipids to the entire external lipid may preferably equal to or less than 1/2, and the molar ratio of DPPE/DOPE, DSPC/DPPE or DSPC/DOPE may preferably range between 1:13:0. Further, the cholesterol content of the external lipid may preferably equal to or greater than 1/3 of the external lipid.

According to the preparation method of the present invention, the PEG-PE of the external lipid plays a role of increasing stability of the liposome in the blood, and may preferably be contained in the molar ratio of 1/6 to 1/4 to the entire external lipid.

According to the preparation method of the present invention, the PEG-PE may additionally include a functional PEG-PE. The functional PEG-PE may include miPEG-PE, or caPEG-PE, but not limited thereto. The functional PEG-PE content may preferably equal to or less than 1/60 to the entire external lipid.

Next, the step 3 prepares the asymmetric liposome encapsulating therein nucleic acid and/or hydrophilic anionic compound, by mixing the internal and external inverse micelles respectively prepared at steps 1 and 2, evaporating organic solvent and performing dialysis.

The preparation method according to the present invention may additionally include a step of attaching a function group to a surface of the prepared liposome for the purpose of cell target-oriented transmission and cell permeation.

According to one embodiment, since the asymmetric liposome for encapsulating nucleic acid has an exterior formed from neutral or anionic lipid which is less toxic and an interior formed from cationic lipid which is toxic but is more advantageous for encapsulating nucleic acid, thereby minimizing damage due to toxicity, stability of liposome in the blood increases due to the presence of PEG-PE as the external lipid, and delivery of a target-oriented material (e.g., antibody, peptide, low molecular ligand, etc.) or cell permeation is facilitated by attaching the target-oriented material to functional group.

In one embodiment, the asymmetric nucleic acid-encapsulating liposome and hydrophilic anionic compound with high efficiency can be used for various purposes including genetic treatment, and drug delivery or imaging using hydrophilic anionic drug delivery and fluorescent contrast agent, which are generally hardly prepared into prodrug.

Certain Examples of the present invention will be explained below to further elucidate the invention, but the inventive concept of the present invention is not limited to any specific example.

Example 1

Preparation of Nucleic Acid-Encapsulating Liposome 1

Nucleic acid-encapsulating liposome was prepared according to a method of the present invention illustrated in FIG. 3.

To be specific, the internal cationic lipid was prepared as follows: Mixed lipid liquid (lipid 1 mg) containing dioleoyl dimethylammonium-propane (DODAP) mixed with dioleoyl phosphatidylethanolamine (DOPE) in a ratio of 1:1 was formed into a thin membrane and completely dried, and suspension was prepared by adding 100 μg of siRNA (N/P ratio=2) with SEQ ID NO: 1/2 to 150 μg 100 mM citric acid buffer solution (pH 4). An inverted micelle encapsulating therein siRNA was then prepared by adding 400 μl diethylether to the suspension and stirring by a bath type sonicator.

The external lipid was prepared as follows. Mixed lipid liquid (lipid; 1.7 mg) of distearoyl phosphatidylcholine:dioleoyl phosphatidylethanolamine:methoxy PEG2000-distearoylphosphatidyl ethanolamine:cholesterol, mixed in molar ratio of DSPC:DOPE:PEG-PE:CH=1.5:1.5:1:2, was formed into a thin membrane and completely dried, and 200 μl of HBS (20 mM HEPES, 150 mM sodium chloride, pH 7.3~7.5) and 120 μl of ethanol were added to form a suspension. An external inverted micelle was then prepared by adding 600 μl ether and stirring with a bath type sonicator. After that, the internal inverted micelle liquid encapsulating therein nucleic acid and external inverted micelle liquid were mixed in a ratio of internal lipid:external lipid=1:1.21, organic solvent was evaporated, and asymmetric siRNA-encapsulating liposome was prepared after removing remaining organic solvent by the HBS dialysis.

Experimental Example 1

Analysis of siRNA Encapsulation Rate According to Compositions of Internal Lipid and Buffer siRNA-encapsulating liposome was prepared in the same manner as that of Example 1, except for preparing the internal cationic lipid as follows. Mixed lipid liquid (lipid 1 mg) of dioleoyl phosphatidylethanolamine (DOPE), mixed with dioleoyl dimethylammonium-propane (DODAP) or dioleoyltrimethylammonium-propane (DOTAP) in a ratio of 1:1 to 9:1, was formed into a thin membrane and completed dried, and suspension was prepared by adding 100 μg of siRNA (N/P ratio=2~4) with SEQ ID NO: 1/2 to 150 μl of 50-150 mM citric acid buffer solution (pH 4 or 5).

Compositions and ratios of the internal and external lipids of the liposome, and compositions and pH of the buffer solution are listed below.

TABLE 1

| | Internal lipid | | External lipid | | Buffer solution | |
|---|---|---|---|---|---|---|
| | Composition | Ratio | Composition | Ratio | Composition | Ratio |
| a | DODAP/DOPE | 1/1 | DSPC/DOPE/PEG-PE/CHOL | 1.5/1.5/1/2 | 0.15M citric acid | 4.0 |
| b | DOTAP/DOPE | 1/1 | DSPC/DOPE/PEG-PE/CHOL | 1.5/1.5/1/2 | 0.15M citric acid | 4.0 |
| c | DODAP/DOPE | 1/1 | DSPC/DOPE/PEG-PE/CHOL | 1.5/1.5/1/2 | 0.15M citric acid | 4.0 |
| d | DODAP/DOPE | 1/1 | DSPC/DOPE/PEG-PE/CHOL | 1.5/1.5/1/2 | 0.15M citric acid | 5.0 |

Figure 4:
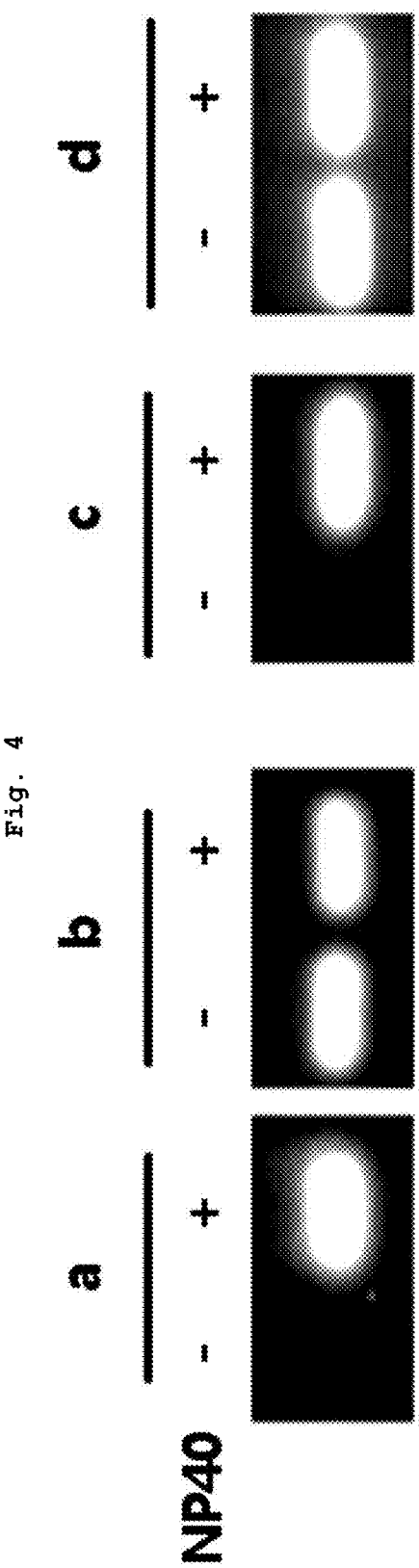
FIG. 4 shows agarose gel electrophoresis image to indicate influence of internal positive charge lipid and pH on the encapsulation of siRNA, in which NP-40 represents non-treated group (−) and siRNA treated group (+) represents the entire siRNA.

The siRNA encapsulation rate of the liposome prepared as explained above was measured by 4% agarose electrophoresis, using 0.5×TBE buffer solution [5.4 g Tris base, 2.75 g boric acid, 2 ml 0.5 M ethylendiamine tetraacetic acid (pH 8.0)) dissolved in 1 l water], and the measurement is provided in FIG. 4.

Referring to FIG. 4, nonidet-P40(NP40) is added to analyze the amount of the entire siRNA. The band appearing when there is no NP40 represents un-encapsulated siRNA.

As a result of measurement, it was confirmed that ethanol, added in the preparation of micelle, helped formation of external inverted micelle encapsulating therein PEG-PE, and the inverted micelle was not formed when ethanol was not used (Result will not be specified). Referring to FIGS. 4(a) and 4(c), good encapsulation rate was obtained when the buffer solution had pH 4, and DODAP was used for the internal cationic lipid, and the concentration of buffer solution did not give noticeable influence. On the contrary, i.e., referring to FIG. 4(b), siRNA was not encapsulated when DOTAP was used for the internal cationic lipid, and referring to FIG. 4(d), the siRNA encapsulation was also not occurred, when buffer solution pH 5 was used in the preparation of the internal inverted micelle.

From the above findings, it was confirmed that, in preparing a liposome according to the preset invention, DODAP is preferably used for the internal cationic lipid for the encapsulation of nucleic acid, and buffer solution preferably has pH 4.

Experimental Example 2

Analysis of siRNA Encapsulation Rate According to External Lipid Composition

The nucleic acid-encapsulating liposome was prepared in the same way as Example 1, except for the differences that internal lipid was fixed as DODAP and DOPE, and immobilized in 150 mM citric acid buffer solution, pH 4, and that certain composition of the external lipid, i.e., phosphatidylcholine/phosphatidyl ethanolamine (PC/PE) was varied as indicated in Table 2. The siRNA encapsulation rate of the liposome was measured by the same method as Example 1 and the result is provided in FIG. 5.

Referring to Table 2, DPPC stands for dioleylphosphatidylcholine, DOPC is dioleylphosphatidylcholine, DSPC is distearoyl phosphatidylcholine, DPPE is dipalmitoylphosphatidyl ethanolamine, and DOPE is dipalmitoylphosphatidyl ethanolamine.

TABLE 2

| | Internal lipid | | External lipid | |
|---|---|---|---|---|
| | Composition | Ratio | Composition | Ratio |
| A | DODAP/DOPE | 1/1 | DPPC/DOPE/PEG-PE/CHOL | 1.5/1.5/1/2 |
| b | DODAP/DOPE | 1/1 | DPPC/DPPE/PEG-PE/CHOL | 1.5/1.5/1/2 |
| c | DODAP/DOPE | 1/1 | DSPC/DPPE/PEG-PE/CHOL | 1.5/1.5/1/2 |
| d | DODAP/DOPE | 1/1 | DOPC/DPPE/PEG-PE/CHOL | 1.5/1.5/1/2 |
| e | DODAP/DOPE | 1/1 | DSPC/DOPE/PEG-PE/CHOL | 1.5/1.5/1/2 |

Figure 5:
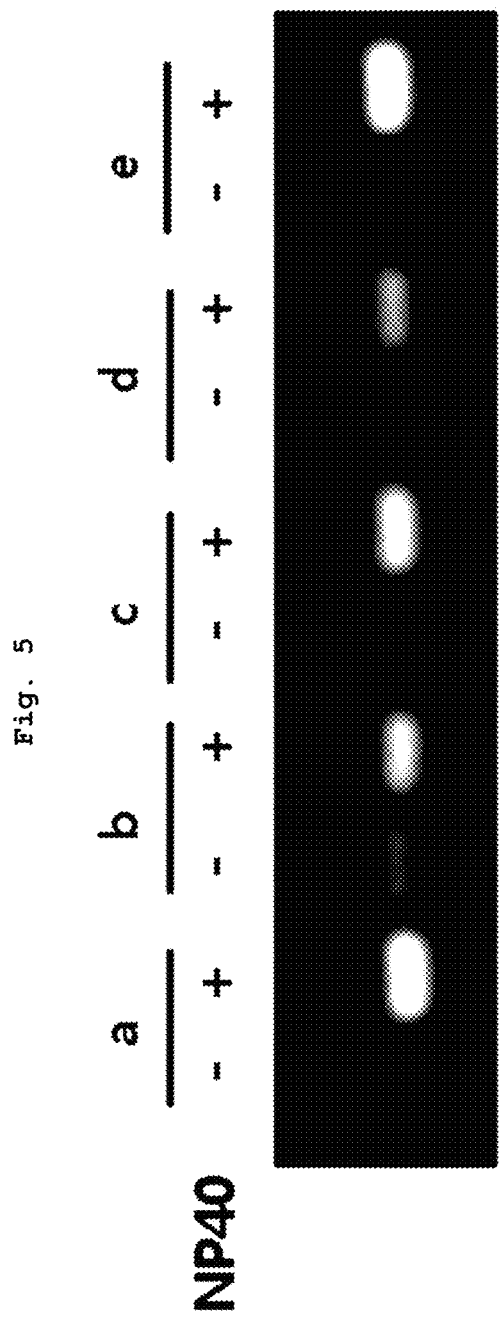
FIG. 5 is an image showing influence of a phosphatidylcholine/phosphatidylethanolamine composition on the encapsulation of nucleic acid.

Referring to FIG. 5, the measured result indicates lower encapsulation when dioleylphosphatidylcholine/dipalmitoylphosphatidyl ethanolamine (DPPC/DPPE) and dioleylphosphatidylcholine/dipalmitoylphosphatidyl ethanolamine (DOPC/DPPE) combination was used in the phosphatidylcholine/phosphatidylethanolamine (PC/PE) composition (FIG. 5 b, d), while the other combinations, i.e., dipalmitoylphosphatidyl ethanolamine/dioleoyl phosphatidylethanolamine (DPPE/DOPE), distearoyl phosphatidylcholine/dipalmitoylphosphatidyl ethanolamine (DSPC/DPPE) and distearoyl phosphatidylcholine/dioleoyl phosphatidylethanolamine (DSPC/DOPE) exhibited high encapsulation rate exceeding 90% (see FIG. 5 a, c, e).

From the above result, it was confirmed that DPPE/DOPE, DSPC/DPPE or DSPC/DOPE combination is more preferred for the external lipid for higher encapsulation rate of nucleic acid in the preparation of liposome according to the present invention.

The nucleic acid-encapsulating liposome was prepared in the same way as Example 1, except for the differences that the external neutral lipid combination was fixed as the DSPC/DOPE combination and that the cholesterol (CHOL) composition was varied as indicated in Table 3. The siRNA encapsulation rate of the liposome was measured by the same method as Example 1 and the result is provided in FIG. 6.

TABLE 3

| | Internal lipid | | External lipid | |
|---|---|---|---|---|
| | Composition | Ratio | Composition | Ratio |
| a | DODAP/DOPE | 1/1 | DSPC/DOPE/PEG-PE/CHOL | 1.75/1.75/1/1 |
| b | DODAP/DOPE | 1/1 | DSPC/DOPE/PEG-PE/CHOL | 1.5/1.5/1/2 |
| c | DODAP/DOPE | 1/1 | DSPC/DOPE/PEG-PE/CHOL | 1.5/1.5/1/3 |

Figure 6:
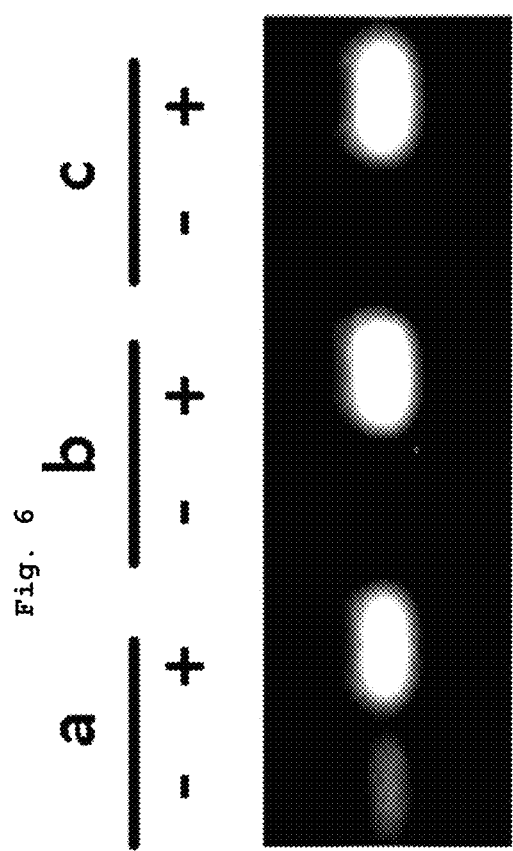
FIG. 6 is an image showing influence of the molar ratio of cholesterol of the external lipid on the encapsulation of nucleic acid.

Referring to FIG. 6, the encapsulation rate decreased when cholesterol was used in a 1/6 molar ratio per the entire external lipid, but the encapsulation rate exceeded 95% when the cholesterol was used in a molar ratio ranging between 1/3 and 1/2.

From the above finding, it was confirmed that the molar ratio of cholesterol per the entire external lipid preferably ranges between 1/3 and 1/2 when preparing nucleic acid-encapsulating liposome.

Further, except for differences that the external lipid neutral lipid combination was fixed as DSPC/DOPE and that the ratio of DSPC/DOPE was varied as presented in Table 4 below, nucleic acid-encapsulating liposome was prepared in the same manner of Example 1 and the siRNA encapsulation rate of the liposome was measured by the same manner of Example 1 and provided in FIG. 7.

TABLE 4

| | Internal lipid | | External lipid | |
|---|---|---|---|---|
| | Composition | Ratio | Composition | Ratio |
| a | DODAP/DOPE | 1/1 | DSPC/DOPE/PEG-PE/CHOL | 3/0/1/2 |
| b | DODAP/DOPE | 1/1 | DSPC/DOPE/PEG-PE/CHOL | 2.5/0.5/1/2 |
| c | DODAP/DOPE | 1/1 | DSPC/DOPE/PEG-PE/CHOL | 2/1/1/2 |
| d | DODAP/DOPE | 1/1 | DSPC/DOPE/PEG-PE/CHOL | 1.5/1.5/1/2 |

Figure 7:
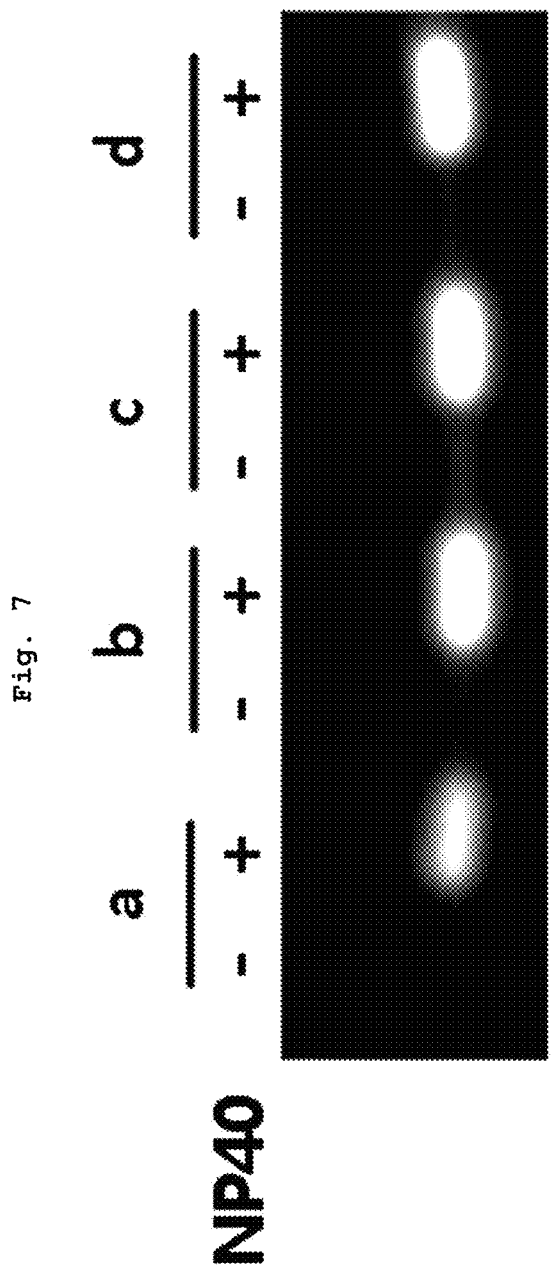
FIG. 7 is an image showing influence of ratio of distearoyl phosphatidylcholine (DSPC) dipalmitoylphosphatidyl ethanolamine (DOPE) of the external lipid on the encapsulation of nucleic acid.

Referring to FIG. 7, when the molar ratio of DSPC:DOPE was adjusted to 1/4:1/4 to 1/2:0 per the entire external lipid and the encapsulation ratio was measured, all the cases exhibited siRNA encapsulation rate exceeding 90%.

Based on the above experiment, it was confirmed that most siRNA was encapsulated when DSPC/DOPE/PEG-PE/CH was selected as the external lipid, with the composition of DSPC in molar ratio of 1/4 to 1/2 per external lipid, DOPE in molar ratio of 0 to 1/4, PEG-PE in molar ratio of 1/6 and cholesterol in molar ratio of 1/3 to 1/2.

Experimental Example 3

Analysis of Encapsulation Rate According to Introduction of Function Group into External Lipid Referring to FIG. 5, nucleic acid-encapsulating liposome was prepared in the same manner as Example 1, except for differences that PEG-PE/maleimide-PEG-PE or PEG-PE/carboxylic-PEG-PE, instead of PEG-PE, was mixed in ratio of 9:1 and that various siRNA (SEQ ID NOS: 1/2, 3/4 and 5/6) were used to introduce function group for binding cell-penetrating peptide to the surface of liposome. The siRNA encapsulation rate of the liposome was measured in the same manner as Example 1 and the result is provided in FIG. 8.

TABLE 5

| | Internal lipid | | External lipid | |
|---|---|---|---|---|
| | composition | ratio | Composition | Ratio |
| a | DODAP/DOPE | 1/1 | DSPC/DOPE/PEG-PE/miPEG-PE/CHOL | 2/1/0.9/0.1/2 |
| b | DODAP/DOPE | 1/1 | DSPC/DOPE/PEG-PE/caPEG-PE/CHOL | 2/1/0.9/0.1/2 |
| c | DODAP/DOPE | 1/1 | DSPC/DOPE/PEG-PE/CHOL | 2/1/1/2 |

Figure 8:
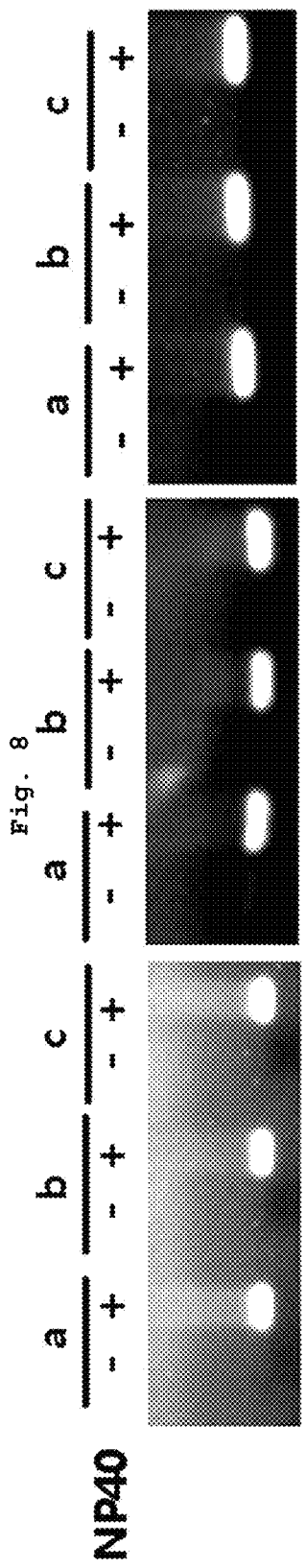
FIG. 8 are images showing influence of polyethylenegrlycol-phosphatidyl ethanolamine (PEG-PE; left), maleimide PEG-PE (miPEG-PE; middle) and carboxylated PEG-PE (caPEG-PE; right) of the external lipid with a function group on the encapsulation of nucleic acid.

Referring to FIG. 8, all the siRNA encapsulation rates exceeded 95%, irrespective of whether the function group was introduced into the surface of the liposome or not. Accordingly, it was confirmed that function group can be additionally introduced to the surface of liposome for cell permeation according to the present invention.

Example 2

Preparation of Liposome Encapsulating Therein Hydrophilic Anionic Compound

Liposome encapsulating therein hydrophilic anionic compound was prepared in the same manner as Example 1, except for the differences that the internal lipid was DODAP:DOPE=1:1 in molar ratio, that the external lipid was DSPC:DOPE:PEG-PE:CHOL=2:1:1:2 in molar ratio, that the molar ratio of external lipid per whole interior was 1:1.2, and that 100 μg or 30 μg of calcein, i.e., anionic fluorescent material, was used for hydrophilic anionic compound instead of nucleic acid.

Example 3

Preparation 2 of Liposome Encapsulating Therein Hydrophilic Anionic Compound

Liposome encapsulating therein hydrophilic anionic compound was prepared in the same manner as Example 1, except for the differences that 100 μg, 30 μg or 10 μg of indocyanine green (ICG), i.e., anionic fluorescent material, was used for hydrophilic anionic compound.

Example 4

Preparation 3-4 of Liposome Encapsulating Therein Hydrophilic Anionic Compound

Liposome encapsulating therein hydrophilic anionic compound was prepared in the same manner as Example 2 or 3, except for the difference that PEG-PE/miPEG-PE, instead of PEG-PE, was used in the ratio of 9:1 for binding cell-penetrating peptide to an exterior.

Example 5

Preparation 5-6 of Liposome Encapsulating Therein Hydrophilic Anionic Compound

Liposome encapsulating therein hydrophilic anionic compound was prepared in the same manner as Example 2 or 3, except for the difference that PEG-PE/caPEG-PE, instead of PEG-PE, was used in the ratio of 9:1 for binding cell-penetrating peptide to an exterior.

Experimental Example 4

Analysis of Encapsulation of Hydrophilic Anionic Compound by Liposome

Fluorescent material-encapsulated liposome is a useful tool to analyze target-oriented transmission and cell permeation of the liposome. The fluorescent material encapsulation rate of liposome according to the present invention was measured as explained below.

The rate of fluorescent material-encapsulated liposome was measured by measuring non-encapsulated fluorescent material with dialysis of liposome encapsulating therein hydrophilic anionic compound prepared at Examples 2-5.

Figure 9:
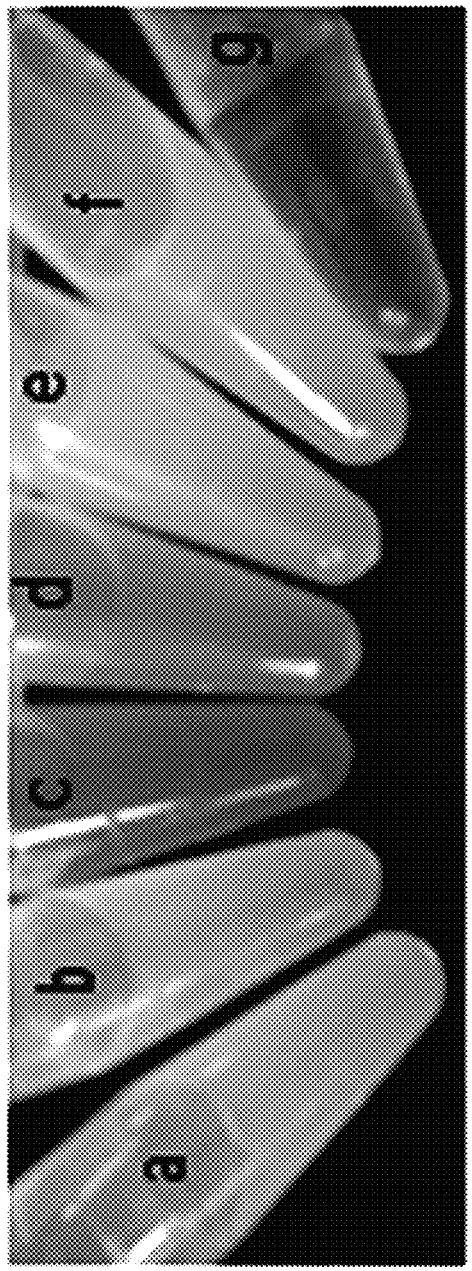
FIG. 9 is an image showing the color distribution of liposome encapsulating therein fluorescent materials and siRNA according to an embodiment of the present invention.
Figure 10:
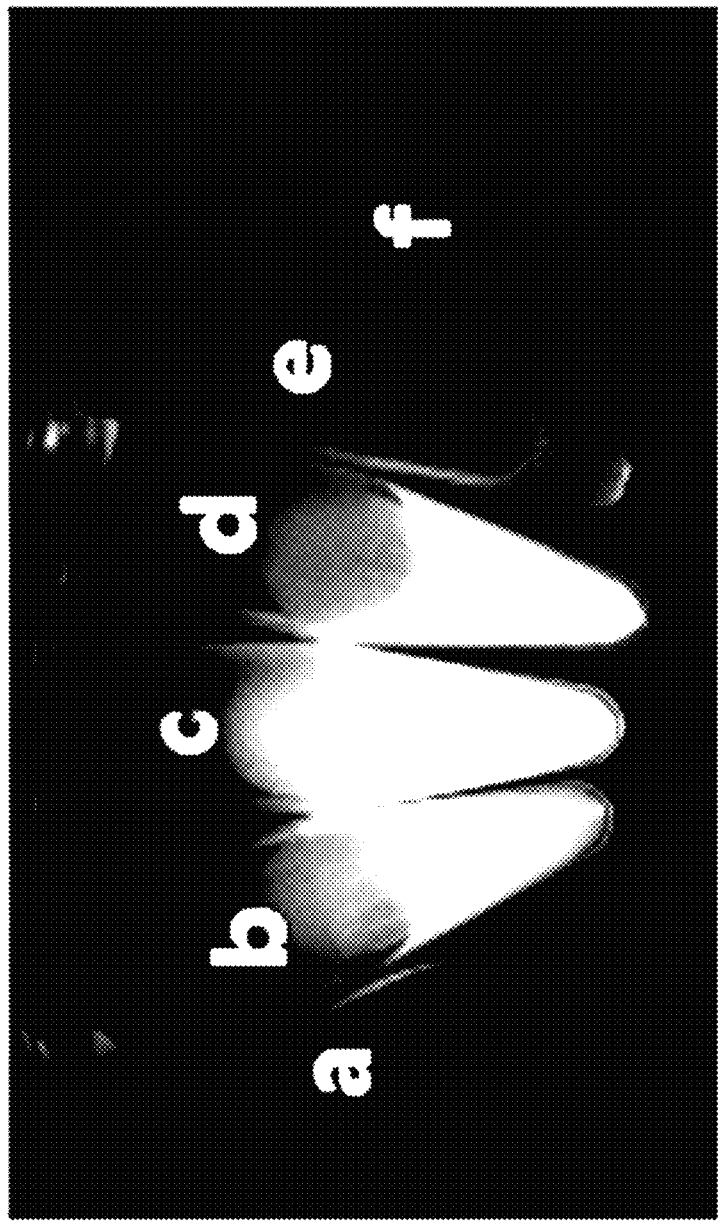
FIG. 10 shows near-infrared fluorescence distribution according to ICG concentration of indocyanine green (ICG)-encapsulating liposome according to an embodiment of the present invention.
Figure 11:
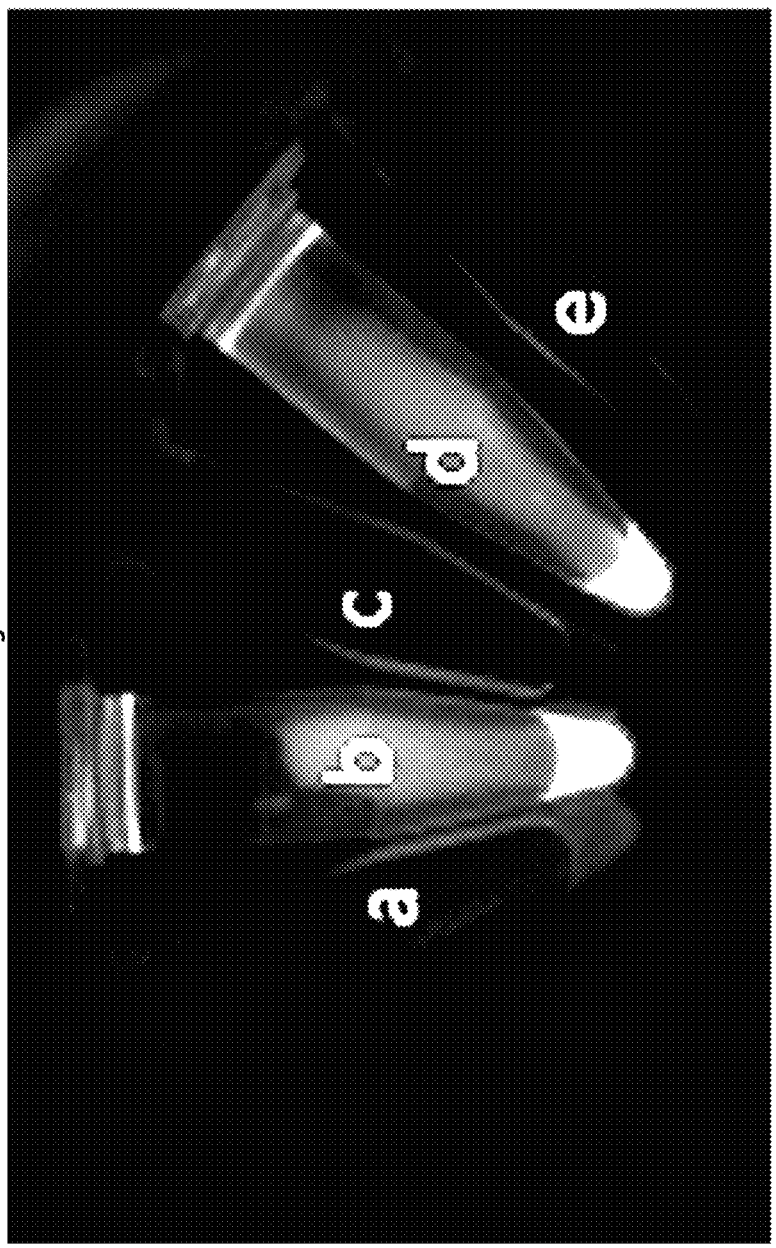
FIG. 11 shows near-infrared fluorescence image taken before (a,c) and after (b,d) disrupting ICG-encapsulating liposome according to an embodiment of the present invention.

The results are provided in FIGS. 9 to 11.

As a result of measuring, all the cases, irrespective of presence or absence of function groups, exhibited encapsulation rate exceeding 95% (Result will not be specified).

FIG. 9 shows liposome encapsulating therein hydrophilic anionic fluorescent material, in which FIG. 9(a) is liposome encapsulating therein 100 μg calcein, FIG. 9(b) is liposome encapsulating therein 30 μg of calcein, FIG. 9(c) is liposome encapsulating therein 100 μg of ICG, FIG. 9(d) is liposome encapsulating therein 30 μg of ICG, FIG. 9(e) is liposome encapsulating therein 10 μg of ICG, FIG. 9(f) is siRNA-encapsulating liposome, and FIG. 9(g) is buffer solution.

FIG. 10 shows the result of exciting ICG ((a) 0 μg, (b) 2 μg, (c) 5 μg, (d) 10 μg, (e) 30 μg, and (f) 100 μg) encapsulated in liposome at 775±5 nm, and measuring fluorescence at 845±7.5 nm, emission wavelength, in which the fluorescence was the highest when ICG concentration within liposome was 5 μg, followed by 2 μg, 10 μg, 30 μg in order. No fluorescence appeared at 100 μg. This shows the fact that ICG has the fluorescent suppressive property at high concentration.

FIG. 11 shows the result of diluting liposome encapsulating therein 30 μg and 100 μg ICG with PBS in 1/3 and 1/10, respectively, and analyzing fluorescence thereof, in which FIGS. 11(a) and 11(b) are fluorescence microscopic (FM) images obtained before and after disrupting liposome encapsulating therein 30 μg ICG with NP40, respectively, and FIGS. 11(c) and 11(d) are FM images obtained before and after disrupting liposome encapsulating therein 100 μg ICG with NP40, respectively.

Referring to FIG. 11, no effect of dilution was visible (FIGS. 11(a), (c)), but strong fluorescence appeared when liposome was lysed in NP40 (FIGS. 11(b), (d)).

The above result indicates the fact that the liposome according to the embodiment is rather advantageous for the purpose of disease diagnosis. That is, liposome designed to encapsulate therein high concentration of ICG and to disintegrate specifically to a disease site such as cancer can be advantageously used in the diagnosis of disease in vivo, by releasing ICG at the disease site such as cancer.

Example 6

Preparation of Liposome Encapsulating Therein Both siRNA and Fluorescent Material at the Same Time Liposome encapsulating therein hydrophilic anionic compound was prepared in the same manner as Example 1, except for the difference that the compositions of the internal and external lipids were varied as indicated in Tables 6 to 8, that the molar ratio of the external lipid was 1:1.2, and that 100 µg siRNA was mixed with 0~100 µg fluorescent material.

TABLE 6

| Internal lipid | | External lipid | | Encapsulated |
|---|---|---|---|---|
| Composition | Ratio | Composition | Ratio | material |
| a | DODAP/DOPE | 1/1 | DSPC/DOPE/PEG-PE/miPEG-PE/CHOL | 1.5/1.5/0.9/0.1/2 | Calcein 30 µg + siRNA 100 µg |
| b | DODAP/DOPE | 1/1 | DSPC/DOPE/PEG-PE/miPEG-PE/CHOL | 1.5/1.5/0.9/0.1/2 | siRNA 100 µg |

TABLE 7

| Internal lipid | | External lipid | |
|---|---|---|---|
| Composition | Ratio | Composition | Ratio |
| a | DODAP/DOPE | 9/1 | DSPC/DOPE/PEG-PE/miPEG-PE/CHOL | 2/1/0.9/0.1/2 |
| b | DOTAP/DOPE | 9/1 | DSPC/DOPE/PEG-PE/caPEG-PE/CHOL | 2/1/0.9/0.1/2 |
| c | DODAP/DOPE | 9/1 | DSPC/DOPE/PEG-PE/CHOL | 2/1/1/2 |

TABLE 8

| Internal lipid | | External lipid | | Encapsulated |
|---|---|---|---|---|
| Composition | Ratio | Composition | Ratio | material |
| a | DODAP/DOPE | 9/1 | DSPC/DOPE/PEG-PE/CHOL | 2/1/1/2 | ICG 10 µg + siRNA 100 µg |
| b | DOTAP/DOPE | 9/1 | DSPC/DOPE/PEG-PE/CHOL | 2/1/1/2 | ICG 5 µg + siRNA 100 µg |
| c | DODAP/DOPE | 9/1 | DSPC/DOPE/PEG-PE/CHOL | 2/1/1/2 | ICG 2 µg + siRNA 100 µg |

The prepared liposomes were dialysed, and then non-encapsulated siRNA was measured by 4% agarose gel electrophoresis. The results of the measurements are provided in FIGS. 12 to 14.

Figure 12:
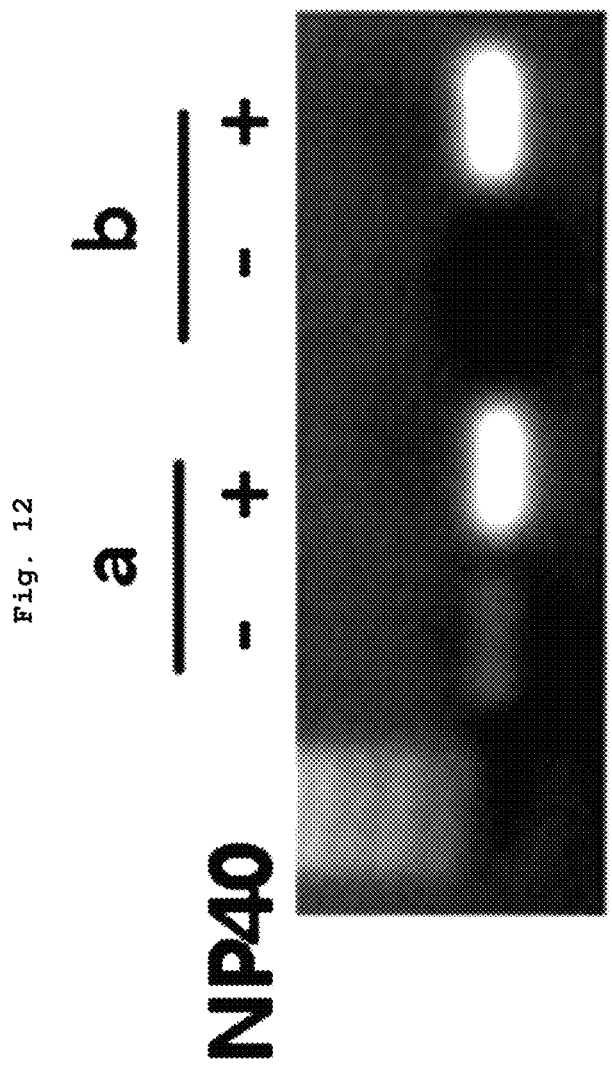
FIG. 12 is an image showing influence of presence/absence of calcein in siRNA on the encapsulation of siRNA in the liposome.
Figure 13:
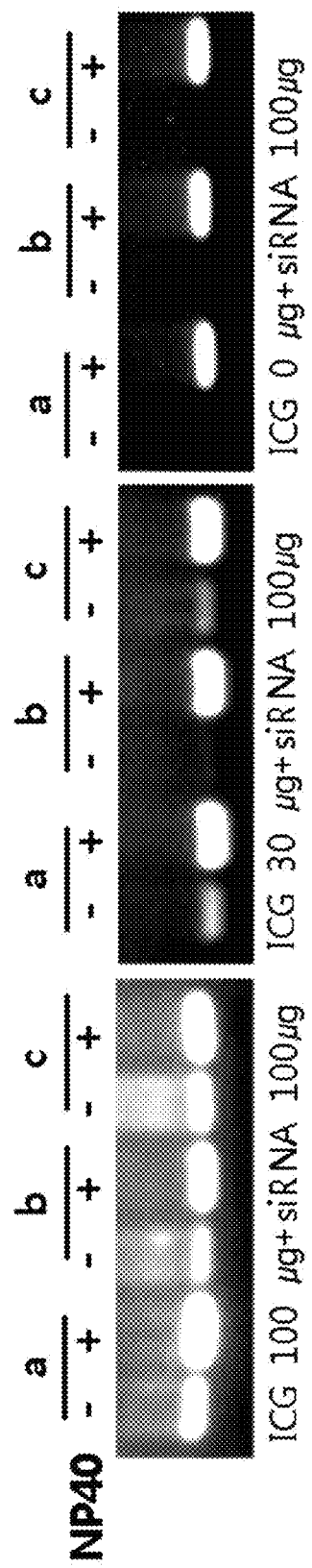
FIG. 13 is images showing liposomes having, on their exteriors, PEG-PE (a), miPEG-PE (b) and caPEG-PE (c), to show influence of ICG concentration on the encapsulation of siRNA in the liposomes.
Figure 14:
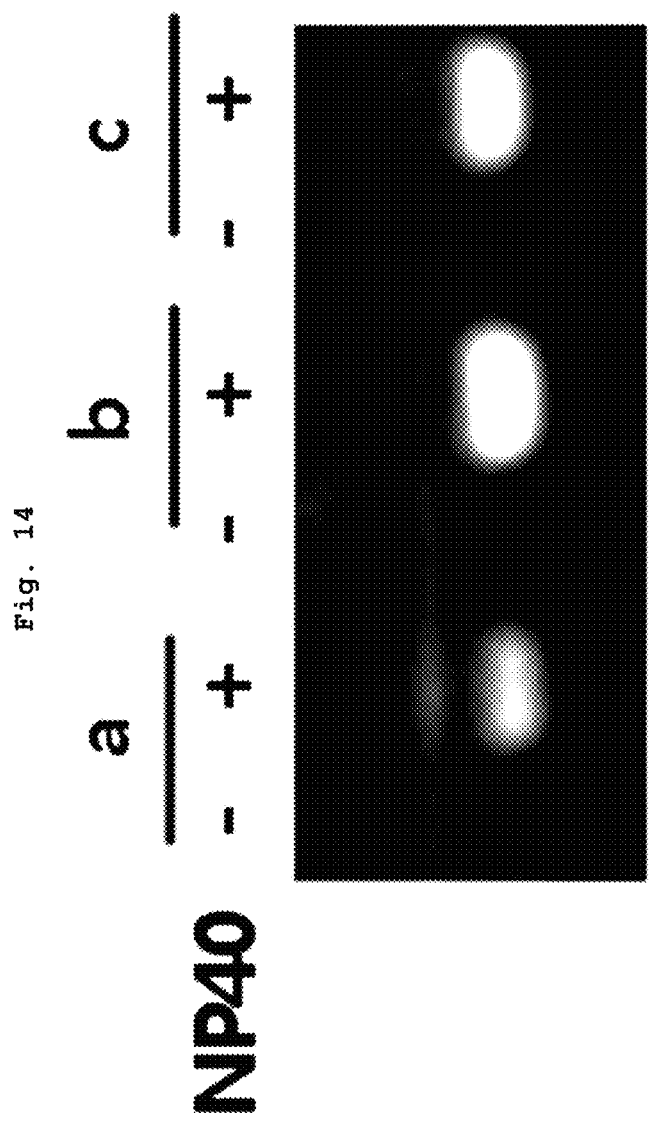
FIG. 14 is an image showing influence on the encapsulation of siRNA in the liposome when treated with lower ICG concentration than FIG. 13.

To be specific, FIG. 12 shows agarose gel electrophoresis image showing siRNA encapsulation rate of liposome with composition of Table 6, FIG. 13 shows agarose gel electrophoresis image showing siRNA encapsulation rate of liposome with composition of Table 7 in which ICG in an amount of 100 µg, 30 µg and 0 µg was mixed with siRNA 100 µg, and FIG. 14 shows agarose gel electrophoresis image showing siRNA encapsulation rate of liposome with composition of Table 8.

As a result of measurement, while the fluorescent material encapsulation rate was highly efficient, irrespective of presence or absence of siRNA, the siRNA encapsulation rate was suppressed dose-dependently (see FIGS. 12 and 13). However, when ICG concentration was limited below 10 µg, no significant influence was observed on the siRNA encapsulation (see FIG. 14).

Experimental Example 5

Figure 15:
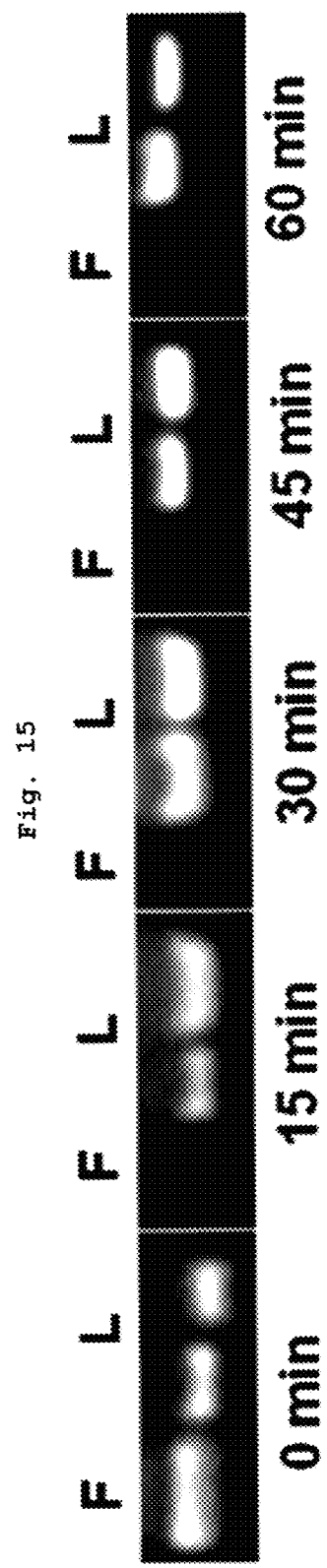
FIG. 15 is analytic images showing the protection siRNA encapsulated in liposome on the disruption of siRNA by RNase A.

Analysis on Protective Effects of siRNA Encapsulating Liposome from RNase A Dissociation When RNase A was high-dose treated on the siRNA-encapsulating liposome with the composition of Table 4 c of Example 2, the protective effects by liposome was analyzed with electrophoresis. After RNase A reaction, the sample was treated with 1% sodium dodecyl sulphate (SDS)+10 mM ethylene diaminetetraacetate (EDTA) to lyse liposome, RNase A activity was inactivated and then electrophoresis was performed. Free siRNA(F), which was not encapsulated in liposome, was completely disintegrated within 15 minutes, whereas siRNA(L) encapsulated in liposome was not disintegrated even after 60 minutes of treatment (FIG. 15).

Experimental Example 6

Analysis of Cytopermeability of Fluorescent Material-Encapsulated Liposome Labeled on its Surface with Cell-Penetrating Peptide To investigate whether the material encapsulated within liposome permeates through the cell and was delivered into protoplasm, sulfhydryl group of the cell-penetrating peptide was conjugated on the maleimide group on the surface of the fluorescent material-encapsulated liposome prepared at Example 2 or 3, and then the cytopermeability and intracellular distribution pattern were analyzed.

FIGS. 16 to 19 show the result of analysis.

Figure 16:
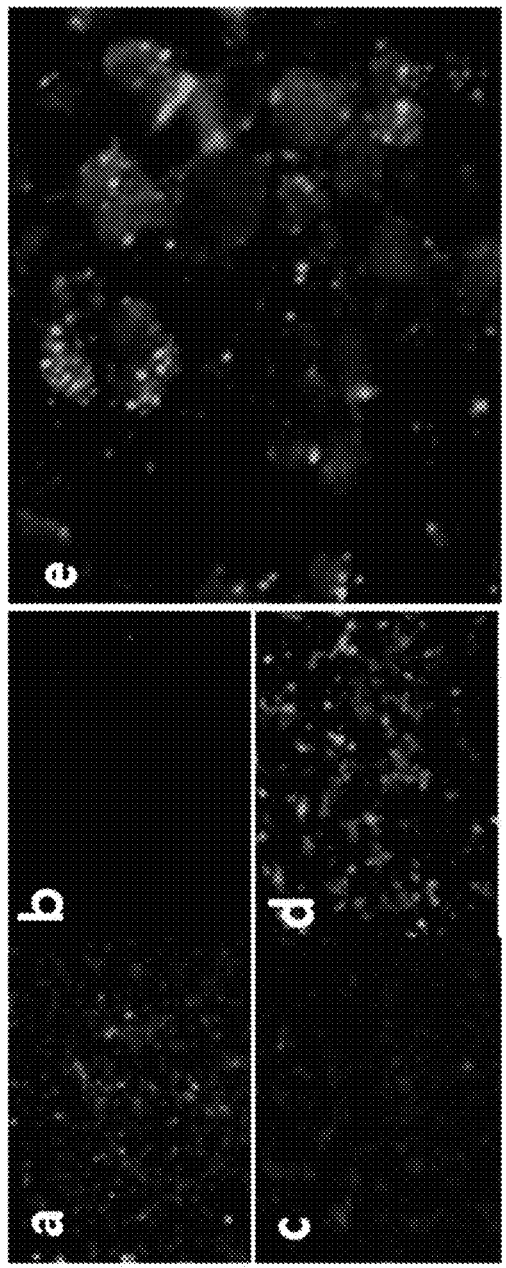
FIG. 16 are analytical images of cell permeation of the calcein-encapsulating liposome into lung cancer cells (A549) without (a and b) or with (c and d) attachment of the R12 peptide on the surface.
Figure 17:
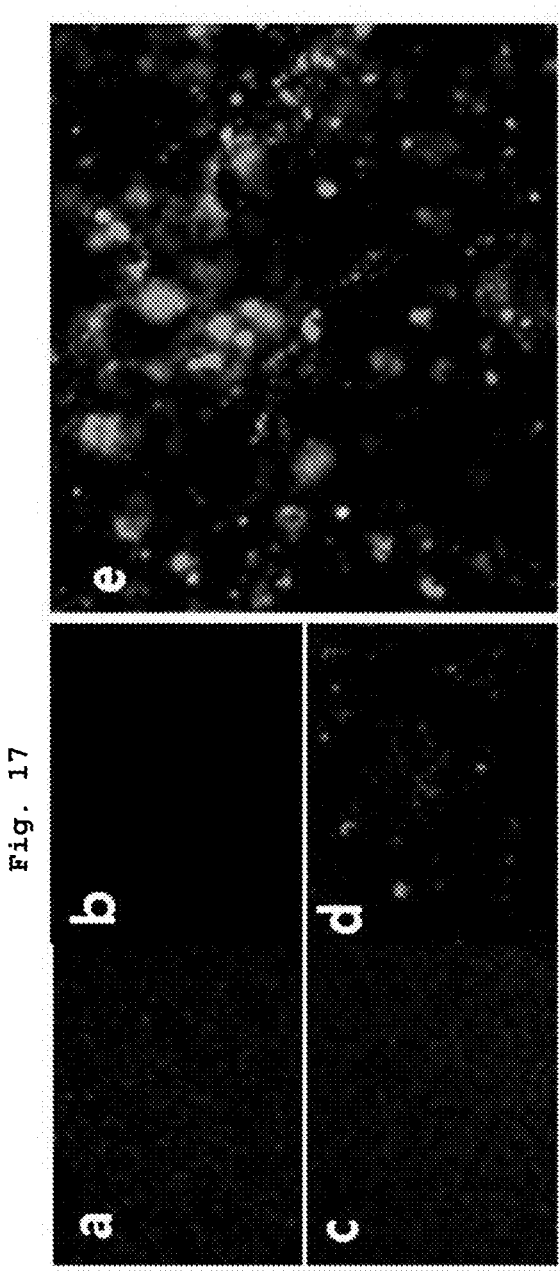
FIG. 17 is analytical images of cell permeation of the calcein-encapsulating liposome into lung cancer cells (NCI-H322) without (a and b) or with (c and d) attachment of the R12 peptide on the surface.

To be specific, FIGS. 16 and 17 are analytic photos of the cytopermeability of A549 and NCI-H322 lung cancer cells (non-small cell lung cancer, NSCLC) according to the presence and absence of the cell-penetrating peptide of the calcein-encapsulating liposome, in which (a) is the DAPI stained nuclei of liposome to which cell-penetrating peptide (R12 peptide (SEQ ID NO: 4)) is not bound, (b) is the fluorescent image of calcein of the liposome to which cell-penetrating peptide is not bound, (c) is the DAPI stained nuclei of the liposome to which cell-penetrating peptide is bound, (d) is fluorescent image of calcein of the liposome to which cell-penetrating peptide is bound, and (e) is an enlarged photo of (d).

Referring to FIGS. 16 and 17, among the calcein-encapsulating liposome, the nonpeptide-labeled liposomes did not display the cytopermeability (see FIGS. 16, 17, b), while the R12 peptide (SEQ ID NO: 7)-labeled liposomes had penetration into A549 and H322 lung cancer cells (non-small cell lung cancer, NSCLC) to display calcein-specific fluorescence in the cell (see FIGS. 16, 17, d). Further, analysis on the calcein fluorescence treated with peptide-binding liposome displayed strong fluorescent particles on the surface. This is the result of attachment of the calcein-encapsulating and peptide-labeled liposome on its surface onto the surface of cell to penetrate according to the peptide labeled on the surface thereof.

Figure 18:
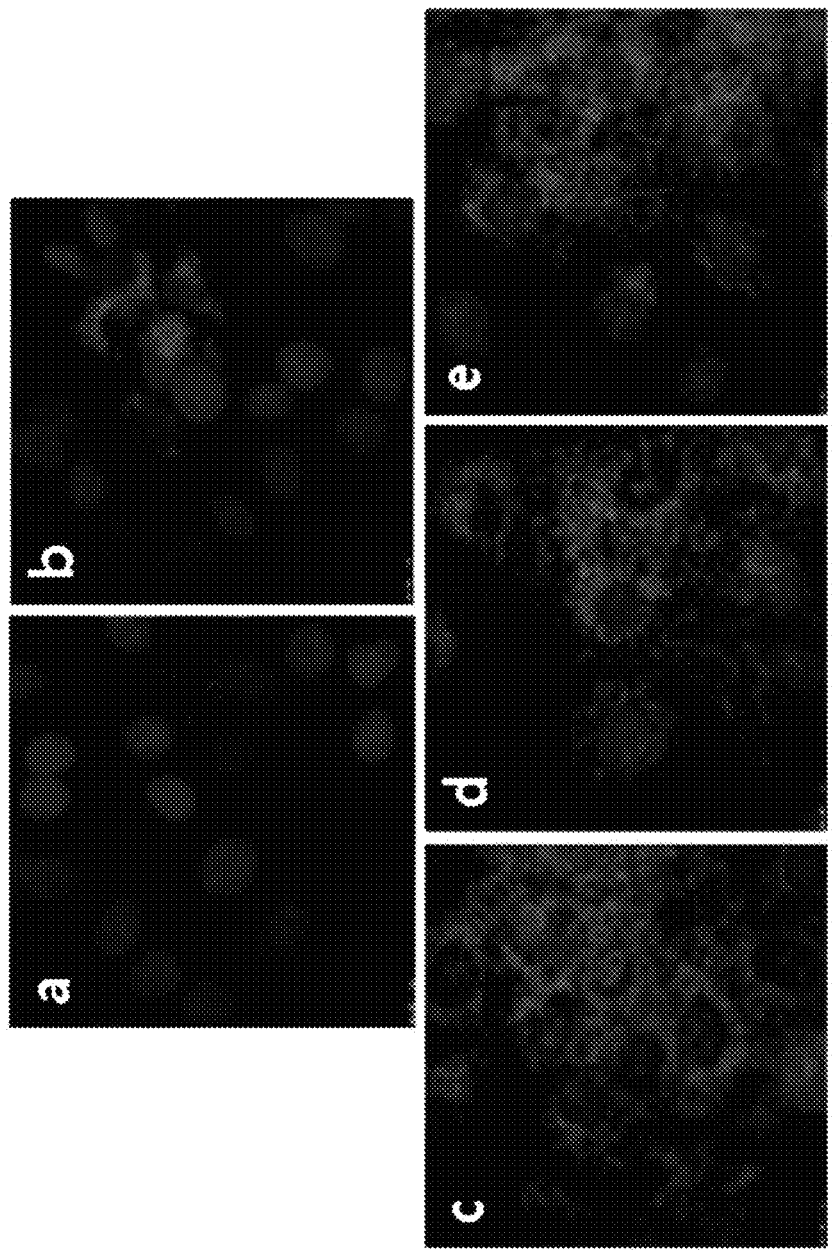
FIG. 18 is images showing A549 cell permeability of the ICG-encapsulating liposomes depending on the absence (b) or presence of the cell penetrating peptides, R8(c), R12(d) and $PC_5$-2(e), attached to the liposome surface.
Figure 19:
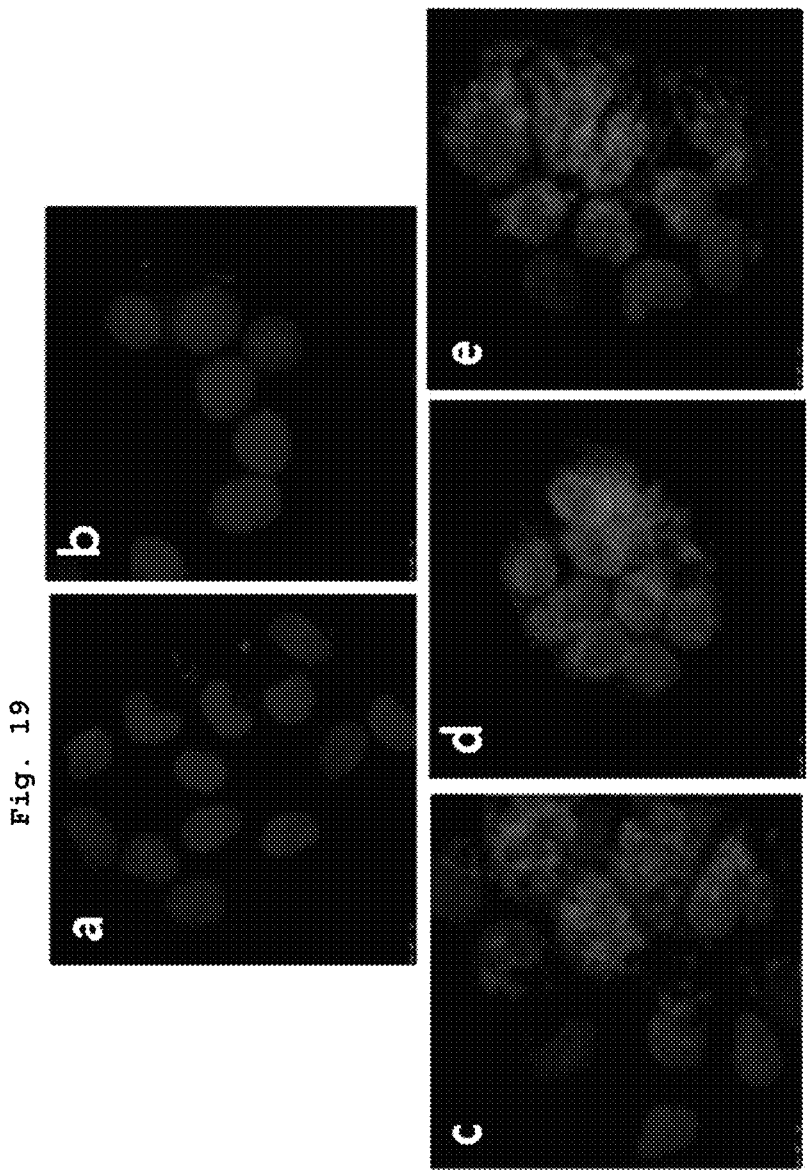
FIG. 19 is images showing NCI-H322 cell permeability of the ICG-encapsulating liposomes depending on the absence (b) or presence of the cell penetrating peptides, R8(c), R12(d) and $PC_5$-2(e), attached to the liposome surface.

FIGS. 18 and 19 show the result of fluorescence microscopic analysis (ex 775±50/em 845±5) on the cytopermeability of ICG-encapsulating liposome which was labeled with R8 (SEQ ID NO: 8), R12 and PC5-2 (SEQ ID NO: 9); Chang et al., *PLos One*, 4, 1-11, 2009), in which (a) is the photo showing the non-treated group with liposome, (b) is DAPI stained nuclei or ICG fluorescent photo of the nonpeptide-binding liposome, (c) is DAPI stained nuclei or ICG fluorescent photo of liposome to which cell-penetrating peptide (R8 (SEQ ID NO: 8)) is bound, (d) is DAPI stained nuclei or ICG fluorescent photo of liposome to which cell-penetrating peptide (R12 (SEQ ID NO: 7)) is bound, and (e) is DAPI stained nuclei or ICG fluorescent photo of liposome to which cell-penetrating peptide (PC5-2 (SEQ ID NO; 9)) is bound.

Referring to FIGS. 18 and 19, although the measurement result varies, all the compositions exhibited peptide dose-dependent permeability with respect to A549 and NCI-H322 cells.

Because asymmetric liposome according to the present invention can penetrate cells, the asymmetric liposome can be advantageously used for delivering the encapsulated material thereof into cytoplasm.

Experimental Example 7

Cytopermeability Analysis on Liposome Encapsulating Therein siRNA and Fluorescent Material, with Cell-Penetrating Peptide-Labeled on the Surface Thereof 0.8 μg pGL3-control plasmid, purchased from Promega (USA), was transfected into A549 cell on 24 well plate with lipofectamine 2000 (LF2K, Invitrogen, USA), and liposome encapsulating therein luciferase siRNA (siGL3, SEQ ID NOS: 10 & 11) with the compositions of Table 5c was treated. Referring to FIG. 20, NT refers to non-treated cell, LF2K refers to positive control transfected with 0.8 μg siGL3, which exhibited approximately 65% suppression of luciferase expression. In the case where the surface of siGL3-encapsulating liposome is treated with 50 μl nonpeptide-labeled liposome in 24 well (siGL3 1 μg), inhibition of expression was not occurred. However, the group treated with 5 μl (1 μg) and 3 μl (0.6 μg) of R12 and R8 peptide-labeled liposome exhibited 30-50% of expression inhibitory effect. On the contrary, as a negative control, the group treated with 5 μl (1 μg) of β-galactosidase siRNA (siβal, SEQ ID NOS: 5 & 6)-encapsulating liposome did not have inhibited luciferase expression.

The foregoing exemplary embodiments and advantages are merely exemplary and are not to be construed as limiting the present invention. The present teaching can be readily applied to other types of apparatuses. Also, the description of the exemplary embodiments of the present inventive concept is intended to be illustrative, and not to limit the scope of the claims.

What is claimed is:

1. A method of preparing an asymmetric liposome, wherein a nucleic acid and/or a hydrophilic anionic compound are encapsulated in an internal aqueous compartment of the liposome, comprising:
  preparing an inner inverted micelle encapsulating the nucleic acid and/or the hydrophilic anionic compound in a cationic lipid and neutral lipid mixture forming an inner layer lipid by use of ether/buffer solution mixture liquid (step 1);
  preparing an outer inverted micelle comprising neutral phospholipids, PEGylated phospholipids and cholesterol as an outer layer lipid by use of ether/alcohol/buffer solution mixture liquid (step 2); and
  preparing the asymmetric liposome encapsulating therein the nucleic acid and/or the hydrophilic anionic compound by mixing the inner inverted micelle and the outer inverted micelle respectively prepared at steps 1 and 2, evaporating organic solvent, and performing dialysis (step 3);
  wherein the inner layer lipid comprises dioleoyl dimethylammonium-propane (DODAP) and dipalmitoylphosphatidyl ethanolamine (DOPE) or dioleoyl phosphatidylethanolamine (DPPE), in a composition ratio of DODAP:DOPE or DPPE=1:1 to 9:1,
  wherein the hydrophilic anionic compound is selected from the group consisting of calcein, indocyanine green and combinations thereof;
  wherein the neutral phospholipids comprise distearoyl phosphatidylcholine/dioleoyl phosphatidylethanolamine (DSPC/DOPE), dipalmitoylphosphatidyl ethanolamine/dioleoyl phosphatidylethanolamine (DPPE/DOPE) or distearoyl phosphatidylcholine/dipalmitoylphosphatidyl ethanolamine (DSPC/DPPE);
  wherein the PEGylated phospholipids comprise polyethyleneglycol-phosphatidylethanolamine (PEG-PE) and functional PEG-PE,
  wherein the functional PEG-PE is PEG-PE which is functionalized with a maleimide or a carboxylic group.

2. The method as set forth in claim 1, wherein the step 1 comprises preparing the inner inverted micelle by suspending the cationic lipid, the neutral lipid and the nucleic acid and/or the hydrophilic anionic compound in a buffer solution pH 4, adding ether and stirring with ultrasonic waves.

3. The method as set forth in claim 1, wherein at step 1, the ratio of negative ion/positive ion (N/P) of the nucleic acid and the cationic lipid in the preparation of the nucleic acid-encapsulating liposome ranges between 1:2 to 1:10 in molar ratio.

4. The method as set forth in claim 1, wherein at step 1, the hydrophilic anionic compound and the nucleic acid are encapsulated individually or simultaneously.

5. The method as set forth in claim 1, wherein step 2 comprises forming the outer inverted micelle by adding the neutral phospholipids, the PEGylated phospholipids and the cholesterol to alcohol and buffer solution and suspending the same, adding ether and stirring with ultrasonic waves.

6. The method as set forth in claim 5, wherein the alcohol and buffer solution has a ratio of 2:1 to 1:1.

7. The method as set forth in claim 5, wherein the alcohol is methanol or ethanol.

8. The method as set forth in claim 5, wherein the molar ratio of the neutral phospholipids to the entire outer layer lipid is equal to or less than 1/2.

9. The method as set forth in claim 5, wherein the molar ratio of the cholesterol to the entire outer layer lipid is equal to or greater than 1/3.

10. The method as set forth in claim 5, wherein the molar ratio of the PEG-PE to the entire outer layer lipid ranges between 1/6 to 1/4, wherein the molar ratio of the functional PEG-PE to the entire outer layer lipid is equal to or less than 1/60.

11. The method as set forth in claim 1, wherein the method further comprises attaching a functional group to a surface of the asymmetric liposome prepared at step 3.

* * * * *

SEQUENCE LISTING

```
<160> NUMBER OF SEQ ID NOS: 11

<210> SEQ ID NO 1
<211> LENGTH: 21
<212> TYPE: RNA
<213> ORGANISM: Artificial Sequence
<220> FEATURE:
<223> OTHER INFORMATION: siRNA1 sense strand
<220> FEATURE:
<221> NAME/KEY: misc_feature
<222> LOCATION: (20)..(21)
<223> OTHER INFORMATION: n is a, c, g, or u

<400> SEQUENCE: 1
cuggccacgu gcaggauuan n                                                    21

<210> SEQ ID NO 2
<211> LENGTH: 21
<212> TYPE: RNA
<213> ORGANISM: Artificial Sequence
<220> FEATURE:
<223> OTHER INFORMATION: siRNA1 antisense strand
<220> FEATURE:
<221> NAME/KEY: misc_feature
<222> LOCATION: (20)..(21)
<223> OTHER INFORMATION: n is a, c, g, or u

<400> SEQUENCE: 2
uaauccugca cguggccagn n                                                    21

<210> SEQ ID NO 3
<211> LENGTH: 25
<212> TYPE: RNA
<213> ORGANISM: Artificial Sequence
<220> FEATURE:
<223> OTHER INFORMATION: siRNA2 sense strand

<400> SEQUENCE: 3
gguucucugc cuguuucgac aacuu                                                25

<210> SEQ ID NO 4
<211> LENGTH: 25
```

```
<212> TYPE: RNA
<213> ORGANISM: Artificial Sequence
<220> FEATURE:
<223> OTHER INFORMATION: siRNA2 antisense strand

<400> SEQUENCE: 4
aaguugucga aacaggcaga gaacc                                           25

<210> SEQ ID NO 5
<211> LENGTH: 21
<212> TYPE: RNA
<213> ORGANISM: Artificial Sequence
<220> FEATURE:
<223> OTHER INFORMATION: siRNA3 sense strand
<220> FEATURE:
<221> NAME/KEY: misc_feature
<222> LOCATION: (20)..(21)
<223> OTHER INFORMATION: n is a, c, g, or u

<400> SEQUENCE: 5
cuuacgcuga guacuucgan n                                               21

<210> SEQ ID NO 6
<211> LENGTH: 21
<212> TYPE: RNA
<213> ORGANISM: Artificial Sequence
<220> FEATURE:
<223> OTHER INFORMATION: siRNA3 antisense strand
<220> FEATURE:
<221> NAME/KEY: misc_feature
<222> LOCATION: (20)..(21)
<223> OTHER INFORMATION: n is a, c, g, or u

<400> SEQUENCE: 6
ucgaaguacu cagcguaagn n                                               21

<210> SEQ ID NO 7
<211> LENGTH: 15
<212> TYPE: PRT
<213> ORGANISM: Artificial Sequence
<220> FEATURE:
<223> OTHER INFORMATION: R12 peptide

<400> SEQUENCE: 7

Arg Arg Arg Arg Arg Arg Arg Arg Arg Arg Arg Arg Gly Gly Cys
1               5                   10                  15

<210> SEQ ID NO 8
<211> LENGTH: 12
<212> TYPE: PRT
<213> ORGANISM: Artificial Sequence
<220> FEATURE:
<223> OTHER INFORMATION: R8 peptide

<400> SEQUENCE: 8

Arg Arg Arg Arg Arg Arg Arg Arg Gly Gly Trp Cys
1               5                   10

<210> SEQ ID NO 9
<211> LENGTH: 15
<212> TYPE: PRT
<213> ORGANISM: Artificial Sequence
<220> FEATURE:
<223> OTHER INFORMATION: PC5-2 peptide

<400> SEQUENCE: 9

Cys Gly Gly Thr Asp Ser Ile Leu Arg Ser Tyr Asp Trp Thr Tyr
1               5                   10                  15
```

```
<210> SEQ ID NO 10
<211> LENGTH: 21
<212> TYPE: RNA
<213> ORGANISM: Artificial Sequence
<220> FEATURE:
<223> OTHER INFORMATION: luciferase siRNA antisense strand
<220> FEATURE:
<221> NAME/KEY: misc_feature
<222> LOCATION: (20)..(21)
<223> OTHER INFORMATION: n is a, c, g, or u

<400> SEQUENCE: 10
ucgaaguacu cagcguaagn n                                          21

<210> SEQ ID NO 11
<211> LENGTH: 21
<212> TYPE: RNA
<213> ORGANISM: Artificial Sequence
<220> FEATURE:
<223> OTHER INFORMATION: luciferase siRNA sense strand
<220> FEATURE:
<221> NAME/KEY: misc_feature
<222> LOCATION: (20)..(21)
<223> OTHER INFORMATION: n is a, c, g, or u

<400> SEQUENCE: 11
cuuacgcuga guacuucgan n                                          21
```